United States Patent
Zang et al.

(10) Patent No.: US 10,280,208 B2
(45) Date of Patent: May 7, 2019

(54) TMIGD2 AND ITS DERIVATIVES AS BLOCKERS OR BINDERS OF CANCER-EXPRESSED HHLA2 FOR IMMUNOTHERAPIES

(71) Applicant: ALBERT EINSTEIN COLLEGE OF MEDICINE, INC., Bronx, NY (US)

(72) Inventors: Xingxing Zang, New York, NY (US); Jordan M. Chinai, Bronx, NY (US); Murali Janakiram, Brooklyn, NY (US); Steven C. Almo, Pelham, NY (US); Andras Fiser, New York, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 15/300,294

(22) PCT Filed: Apr. 24, 2015

(86) PCT No.: PCT/US2015/027429
§ 371 (c)(1),
(2) Date: Sep. 29, 2016

(87) PCT Pub. No.: WO2015/167948
PCT Pub. Date: Nov. 5, 2015

(65) Prior Publication Data
US 2017/0174742 A1    Jun. 22, 2017

Related U.S. Application Data

(60) Provisional application No. 61/986,238, filed on Apr. 30, 2014.

(51) Int. Cl.
*C07K 14/70* (2006.01)
*C07K 14/705* (2006.01)
*A61K 38/00* (2006.01)

(52) U.S. Cl.
CPC ........ *C07K 14/70503* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 9,447,186 B2 | 9/2016 | Zang et al. | |
| 2007/0122406 A1* | 5/2007 | Chamberlain | C07K 16/30 424/144.1 |
| 2016/0002337 A1 | 1/2016 | Zang | |

FOREIGN PATENT DOCUMENTS

| | | | |
|---|---|---|---|
| WO | 2007039507 A2 | 4/2007 | |
| WO | 2011020024 A2 | 2/2011 | |
| WO | WO 2011/020024 * | 2/2011 | ........... C07K 14/705 |
| WO | 2012075184 A2 | 6/2012 | |
| WO | 2013049254 A1 | 4/2013 | |
| WO | 2015094782 A1 | 6/2015 | |
| WO | 2016085662 A1 | 6/2016 | |

OTHER PUBLICATIONS

Zhao et al. (PNAS, 110(24): 9879-9884, 2013).*
Bauer et al. (Cancer, 109(9):1721-1728, 2007).*
International Search Report and Written Opinion, dated Aug. 14, 2015 in connection with PCT International Application No. PCT/US2015/27429, 10 pages.

* cited by examiner

*Primary Examiner* — Nelson B Moseley, II
(74) *Attorney, Agent, or Firm* — Amster, Rothstein & Ebenstein LLP (57) ABSTRACT

Provided are methods of treating an HHLA2-bearing tumor in a subject with a fusion protein comprising an IgV-like domain of a TMIGD2 sufficient to treat the HHLA2-bearing tumor. A fusion protein comprising an IgV-like domain of a TMIGD2 and related compositions and encoding nucleic acids are also provided.

14 Claims, 3 Drawing Sheets
Specification includes a Sequence Listing.

Signal Peptide | IgV-like domain

MGSPGMVLGLLVQIWALQEASSLSVQQGPNLLQVRQGSQATLVC
QVDQATAWERLRVKWTKDGAILCQPYITNGSLSLGVCGPQGRLS
WQAPSHLTLQLDPVSLNHSGAYVCWAAVEIPELEEAEGNITRLF
VDPDDPTQNRNRIASFPGFLPVLLGVGSMGVAAIVWGAWFWGRR

Transmembrane Domain

Cytoplasmic Tail

SCQQRDSGNSPGNAFYSNVLYRPRGAPKKSEDCSGEGKDQRGQS
IYSTSFPQPAPRQPHLASRPCPSPRPCPSPRPGHPVSMVRVSPR
PSPTQQPRPKGFPKVGEE

TMIGD2 AND ITS DERIVATIVES AS BLOCKERS OR BINDERS OF CANCER-EXPRESSED HHLA2 FOR IMMUNOTHERAPIES

CROSS-REFERENCE TO RELATED APPLICATION

This application is a U.S. national stage entry under 35 U.S.C. § 371 of PCT International Patent Application No. PCT/US2015/027429, filed Apr. 24, 2015, which claims the benefit of U.S. Provisional Patent Application No. 61/986,238, filed on Apr. 30, 2014, the contents of which are incorporated herein by reference into the subject application.

STATEMENT OF GOVERNMENT SUPPORT

This invention was made with government support under grant number PC094137 awarded by the Department of Defense. The government has certain rights in the invention.

BACKGROUND OF THE INVENTION

Throughout this application various publications are referred to in parentheses. Full citations for these references may be found at the end of the specification. The disclosures of these publications, and all patents, patent application publications and books referred to herein, are hereby incorporated by reference in their entirety into the subject application to more fully describe the art to which the subject invention pertains.

The B7 and CD 28 families are part of the immune system. The B7 ligand family binds to the CD28 receptor family on T cells and other immune cells, which critically regulates functions of immune cells. The currently known members of the B7 family include B7-1 (CD80), B7-2 (CD86), B7h (CD275), PD-L1 (B7-H1, CD274), PD-L2 (B7-DC, CD273), B7-H3 (CD276), B7x (B7-H4/B7s1) and HHLA2, whereas the CD28 family contains CD28, CTLA-4 (CD152), ICOS (CD278) and PD-1 (CD279)(1-3). The B7/CD28 pathways are very attractive therapeutic targets (3-9). The FDA has approved five new drugs developed from the B7/CD28 families.

HHLA2 has recently been characterized as a member of the B7 family. In 2013, by homology search of various databases using amino acid sequences of human B7x and B7-H3, HERV-H LTR-associating 2 (HHLA2) was identified as a new member of the B7 family (1). The human HHLA2 gene is located in the q13.13 region of the chromosome 3 and is near the B7-1 and B7-2 genes (q13.3-q21). HHLA2 shares varying levels of amino acid similarity with human B7-1 (23%), B7-2 (29%), B7h (30%), PD-L1 (26%), PD-L2 (27%), B7-H3 long form (32%) and short form (33%), and B7x (30%) (1), which are comparable to the homologies exhibited by other members of the family; for example, B7-1, the founding member of the B7 family, shares 22-37% amino acid similarity with other human B7 molecules. HHLA2 protein is expressed on the cell surface and inhibits both human CD4 and CD8 T cell functions (1).

HHLA2 is widely expressed in many human cancers. It was recently shown that HHLA2 protein can be detected in the epithelium of the placenta, gut, kidney, gallbladder and breast, but not in most other organs (10). In contrast, HHLA2 protein was widely expressed in human cancers from the breast, lung, thyroid, melanoma, pancreas, ovary, liver, bladder, colon, prostate, kidney, esophagus and hematological malignancies of leukemia and lymphoma (10). A more detailed analysis was performed on a cohort of 50 patients with triple-negative breast cancer; 56% of patients had aberrant expression of HHLA2 on their tumors. This expression significantly correlated with advanced breast cancer stage and metastatic spread to lymph nodes (10). These results demonstrate that the endogenous HHLA2 protein is absent in most normal tissues, but is widely over-expressed in human cancers. Therefore the HHLA2 pathway represents a novel immunosuppressive mechanism within the tumor microenvironment and is an attractive target for human cancer therapy.

The present invention addresses the need for improved therapies and therapeutics based on the HERV-H LTR Associating Protein 2 (HHLA2) pathway based on identifying a binding partner protein for HHLA2.

SUMMARY OF THE INVENTION

A method of treating an HHLA2-bearing tumor in a subject is provided comprising administering to the subject an amount of a fusion protein comprising an IgV-like domain (or >80% identity) of a TMIGD2 sufficient to treat the HHLA2-bearing tumor.

Also provided is a method of treating an HHLA2-bearing tumor in a subject comprising administering to the subject an amount of an agent comprising an IgV-like domain (or >80% identity) of a TMIGD2 conjugated to a cytotoxic agent, and/or administered in combination with radiation therapy, sufficient to treat the HHLA2-bearing tumor.

Also provided is a method of inhibiting immunosuppression in a subject by an HHLA2-bearing tumor comprising administering an amount of (i) a fusion protein, comprising an IgV-like domain (or >80% identity) of a TMIGD2 and an Fc portion of an immunoglobulin G, or (ii) an amount of a purified protein comprising an IgV-like domain (or >80% identity) of a TMIGD2 but not comprising SEQ ID NO:4, sufficient to inhibit immunosuppression in a subject by an HHLA2-bearing tumor.

Also provided is an isolated fusion protein comprising an IgV-like domain (or >80% identity) of a TMIGD2 and an Fc portion of an immunoglobulin G. Also provided is a composition comprising such a fusion protein. Also provided is an isolated recombinant nucleic acid encoding such a fusion protein. Also provided is a composition comprising such an isolated recombinant nucleic acid encoding such a fusion protein.

DETAILED DESCRIPTION OF THE INVENTION

A method of treating an HHLA2-bearing tumor in a subject is provided comprising administering to the subject an amount of a fusion protein comprising an IgV-like domain (or >80% identity of an IgV-like domain) of a TMIGD2 sufficient to treat the HHLA2-bearing tumor.

In an embodiment, the fusion protein comprising an IgV-like domain of a TMIGD2 comprises an Fc portion of an immunoglobulin G. In an embodiment, the C-terminal residue of the IgV-like domain of a TMIGD2 of the fusion protein is fused via a peptide bond to an N-terminal residue of an Fc portion of an immunoglobulin G. In an embodiment, the immunoglobulin G has the sequence of a human immunoglobulin G. In an embodiment, the immunoglobulin G is an immunoglobulin G1.

Also provided is a method of treating an HHLA2-bearing tumor in a subject comprising administering to the subject an amount of an agent comprising an IgV-like domain (or >80% identity) of a TMIGD2 conjugated to a cytotoxic agent, and/or administered in combination with radiation therapy, sufficient to treat the HHLA2-bearing tumor.

As used herein, "treating" a tumor means that one or more symptoms of the disease, such as the tumor itself, metastasis thereof, vascularization of the tumor, or other parameters by which the disease is characterized, are reduced, ameliorated, prevented, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries. Preferably, the treatment is effective to reduce tumor growth and/or size.

In an embodiment of the methods, the IgV-like domain of a TMIGD2 comprises consecutive amino acid residues having the sequence set forth in SEQ ID NO:3.

Also provided is a method of inhibiting immunosuppression in a subject by an HHLA2-bearing tumor comprising administering an amount of (i) a fusion protein, comprising an IgV-like domain of a TMIGD2 and an Fc portion of an immunoglobulin G, or (ii) an amount of a purified protein comprising an IgV-like domain of a TMIGD2 but not comprising SEQ ID NO:4, sufficient to inhibit immunosuppression in a subject by an HHLA2-bearing tumor.

In an embodiment of the methods, the HHLA2 of the HHLA2-bearing tumor is a human HHLA2.

In an embodiment of the methods, the HHLA2-bearing tumor is a tumor of a breast, lung, thyroid, melanoma, pancreas, ovary, liver, bladder, colon, prostate, kidney, esophagus, or is a hematological tumor. In an embodiment of the methods, the HHLA2-bearing tumor is a hematological tumor and is a leukemia or a lymphoma. In an embodiment of the methods, the HHLA2-bearing tumor is a tumor of the breast and is a triple negative breast cancer.

In an embodiment of the inventions described herein, the fusion protein comprises consecutive amino acid residues having the sequence set forth in SEQ ID NO:2. In an embodiment, the fusion protein comprises consecutive amino acid residues having the sequence set forth in SEQ ID NO:3.

Also provided is an isolated fusion protein comprising an IgV-like domain of a TMIGD2 and an Fc portion of an immunoglobulin G. In an embodiment, the isolated fusion protein comprises SEQ ID NO:2. In an embodiment, the isolated fusion protein comprises SEQ ID NO:3.

An isolated chimeric nucleic acid encoding an isolated fusion protein as described herein is provided.

A composition comprising the isolated fusion protein as described herein and a carrier is provided.

In an embodiment, the composition is a pharmaceutical composition, and the carrier is a pharmaceutical carrier.

The term "TMIGD2-Ig" fusion protein as used herein means a fusion protein constructed of a portion of an immunoglobulin and an active portion of a TMIGD2, or proteins having >80% identical sequence thereto. In a preferred embodiment, the active portion of a TMIGD2 is an extracellular domain of a TMIGD2. In an embodiment, the TMIGD2 has the sequence of a human TMIGD2. In an embodiment, the active portion of a TMIGD2 is the IgV-like domain of an active portion of a TMIGD2. In an embodiment, the portion of an immunoglobulin is a portion of an IgG or an IgM. In an embodiment, it as a portion of an IgG. The IgG portion of the fusion protein can be, e.g., any of an IgG1, IgG2, IgG2a, IgG2b, IgG3 or IgG4 or a portion thereof. In an embodiment, the portion is an Fc region. In an embodiment the fusion protein comprises a sequence identical to an Fc portion of a human IgG1, human IgG2, human IgG2a, human IgG2b, human IgG3 or human IgG4. In an embodiment the fusion protein comprises a sequence identical to an Fc portion of a human IgG1. The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, by recombinantly engineering the nucleic acid encoding the fusion protein.

In an embodiment, the Fc portion of the Ig is used in the fusion protein. The presence of the Fc domain markedly increases the plasma half-life of the attached protein (e.g. the IgV-like domain of the TMIGD2), which prolongs therapeutic activity. In addition, the Fc domain also enables the fusion protein to interact with Fc-receptors. In an embodiment, the TMIGD2-Ig comprises a TMIGD2 portion linked to an Fc domain. In an embodiment, the TMIGD2 portion is bound directly by a peptide bond to the Fc domain. In an embodiment, the TMIGD2 portion is linked to the Fc domain through a linker. In an embodiment, it is linked via a peptide linker which permits flexibility. In an embodiment, the linker is rigid. In an embodiment the linker is cleavable. Non-limiting examples of flexible linkers within the scope of the invention are $G_n$, and GGGGS (SEQ ID NO:7), and (GGGGS)$_n$ (SEQ ID NO:7), where n=2, 3, 4 or 5. Non-limiting examples of rigid linkers within the scope of the invention are EAAAK (SEQ ID NO:8), (EAAAK)$_n$ (SEQ ID NO:8) and (XP)$_n$, where X can be any amino acid. Non-limiting examples of cleavable linkers within the scope of the invention include disulfide links and protease cleavable linkers. In a preferred embodiment, the linker is a peptide linker.

In an embodiment, the Fc domain has the same sequence or 95% or greater sequence similarity with a human IgG1 Fc domain. In an embodiment, the Fc domain has the same sequence or 95% or greater sequence similarity with a human IgG2 Fc domain. In an embodiment, the Fc domain has the same sequence or 95% or greater sequence similarity with a human IgG3 Fc domain. In an embodiment, the Fc domain has the same sequence or 95% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (11, 12).

In an embodiment, the fusion protein described herein is recombinantly produced. In an embodiment, the fusion protein is produced in a eukaryotic expression system. In an embodiment, the fusion protein produced in the eukaryotic expression system comprises glycosylation at a residue on the Fc portion corresponding to Asn297.

In an embodiment, the fusion protein is a homodimer. In an embodiment, the fusion protein is monomeric. In an embodiment, the fusion protein is polymeric.

In an embodiment, of all aspects of the invention described herein reciting a subject, the subject is a human. In an embodiment, of all aspects of the invention described herein reciting HHLA2, the HHLA2 is a human HHLA2.

In an embodiment, the HHLA2 is a human HHLA2 comprising the following sequence: (SEQ ID NO:1)

```
MKAQTALSFFLILITSLSGSQGIFPLAFFIYVPMNEQIVIGRLDE
DIILPSSFERGSEVVIHWKYQDSYKVHSYYKGSDHLESQDPRYAN
RTSLFYNEIQNGNASLFFRRVSLLDEGIYTCYVGTAIQVITNKVV
LKVGVFLTPVMKYEKRNTNSFLICSVLSVYPRPIITWKMDNTPIS
ENNMEETGSLDSFSINSPLNITGSNSSYECTIENSLLKQTWTGRW
TMKDGLHKMQSEHVSLSCQPVNDYFSPNQDFKVTWSRMKSGTFSV
LAYYLSSSQNTIINESRFSWNKELINQSDFSMNLMDLNLSDSGEY
LCNISSDEYTLLTIHTVHVEPSQETASHNKGLWILVPSAILAAFL
LIWSVKCCRAQLEARRSRHPADGAQQERCCVPPGERCPSAPDNGE
ENVPLSGKV.
```

In an embodiment, the TMIGD2-Ig fusion protein comprises the following sequence (SEQ ID NO:2):

```
PNLLQVRQGSQATLVCQVDQATAWERLRVKWTKDGAILCQPYITN
GSLSLGVCGPQGRLSWQAPSHLTLQLDPVSLNHSGAYVCWAAVEI
PELEEAEGNITRLFVDPDDPTQNRNRIASFGGRSKTSGSEPKSCD
KTHTCPPCPAPELLGGPSVFLFPPKPKDTLMISRTPEVTCVVVDV
SHEDPEVKFNWYVDGVEVHNAKTKPREEQYNSTYRVVSVLTVLHQ
DWLNGKEYKCKVSNKALPAPIEKTISKAKGQPREPQVYTLPPSRE
EMTKNQVSLTCLVKGFYPSDIAVEWESNGQPENNYKTTPPVLDSD
GSFFLYSKLTVDKSRWQQGNVFSCSVMHEALHNHYTQKSLSLSPG
K.
```

In a further embodiment, the TMIGD2-Ig fusion protein comprises the following sequence (SEQ ID NO:3):

```
LSVQQGPNLLQVRQGSQATLVCQVDQATAWERLRVKWTKDGAILC
QPYITNGSLSLGVCGPQGRLSWQAPSHLTLQLDPVSLNHSGAYVC
WAAVEIPELEEAEGNITRLFVDPDDPTQNRNRIASFGGRSKTSGS
EPKSCDKTHTCPPCPAPELLGGPSVFLFPPKPKDTLMISRTPEVT
CVVVDVSHEDPEVKFNWYVDGVEVHNAKTKPREEQYNSTYRVVSV
LTVLHQDWLNGKEYKCKVSNKALPAPIEKTISKAKGQPREPQVYT
LPPSREEMTKNQVSLTCLVKGFYPSDIAVEWESNGQPENNYKTTP
PVLDSDGSFFLYSKLTVDKSRWQQGNVFSCSVMHEALHNHYTQKS
LSLSPGK.
```

In an embodiment, the IgV-like domain of TMIGD2 comprises the following sequence (SEQ ID NO:5):

```
PNLLQVRQGSQATLVCQVDQATAWERLRVKWTKDGAILCQPYITN
GSLSLGVCGPQGRLSWQAPSHLTLQLDPVSLNHSGAYVCWAAVEI
PELEEAEGNITRLFVD.
```

In an embodiment, the fusion protein comprises a portion comprising the following sequence including an IgV-like domain of TMIGD2 (SEQ ID NO:6):

```
PNLLQVRQGSQATLVCQVDQATAWERLRVKWTKDGAILCQPYITN
GSLSLGVCGPQGRLSWQAPSHLTLQLDPVSLNHSGAYVCWAAVEI
PELEEAEGNITRLFVDPDDPTQNRNRIASF.
```

In an embodiment, the methods can be performed, *mutatis mutandis*, wherein a nucleic acid encoding a TMIGD2-Ig is administered in a fashion such that it can express inside the subject, in place of the TMIGD2-Ig fusion protein.

Cancers, including tumors, treatable by the invention include e.g. tumors of the nasopharynx, pharynx, lung, bone, brain, salivary gland, stomach, esophagus, testes, ovary, uterus, endometrium, liver, small intestine, appendix, colon, rectum, gall bladder, pancreas, kidney, urinary bladder, breast, cervix, vagina, vulva, prostate, thyroid, and skin, or a glioma. In an embodiment, the cancer treated is a metastatic melanoma. In an embodiment, the cancer treated comprises a tumor. In an embodiment, the cancer treated comprises an HHLA2-bearing tumor.

This invention also provides a composition comprising a fusion protein as described herein. In an embodiment, the composition is a pharmaceutical composition. In an embodiment the composition or pharmaceutical composition comprising one or more of the fusion proteins described herein is substantially pure with regard to the fusion protein. A composition or pharmaceutical composition comprising one or more of the fusion proteins described herein is "substantially pure" with regard to the antibody or fragment when at least about 60 to 75% of a sample of the composition or pharmaceutical composition exhibits a single species of the fusion protein. A substantially pure composition or pharmaceutical composition comprising one or more of the fusion proteins described herein can comprise, in the portion thereof which is the fusion protein, 60%, 70%, 80% or 90% of the fusion protein of the single species, more usually about 95%, and preferably over 99%. Fusion protein purity or homogeneity may be tested by a number of means well known in the art, such as polyacrylamide gel electrophoresis or HPLC.

The invention also encompasses compositions comprising the described fusion proteins and a carrier. The carrier may comprise one or more pharmaceutically-acceptable carrier components. Such pharmaceutically-acceptable carrier components are widely known in the art. Examples of acceptable pharmaceutical carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and heparinized sodium citrate acid dextrose solution. The pharmaceutically acceptable carrier used can depend on the route of administration. The pharmaceutical composition can be formulated for administration by any method known in the art, including but not limited to, oral administration, parenteral administration, intravenous administration, transdermal administration, intramuscular administration, intranasal administration, direct injection into a tumor site, and administration through an osmotic mini-pump.

Cytotoxic agents, as referred to herein, include chemotherapuetic agents. In an embodiment, the cytotoxic agent is doxorubicin. In an embodiment, the cytotoxic agent is a maytansinoid. In an embodiment, the cytotoxic agent an alkylating agent, an anti-metabolite, a plant alkaloid or terpenoid, or a cytotoxic antibiotic. In embodiments, the cytotoxic agent is cyclophosphamide, bleomycin, etoposide, platinum (cisplatin), fluorouracil, vincristine, methotrexate, taxol, epirubicin, leucovorin (folinic acid), or irinotecan. Radiation therapy can be used in place of or in combination with one or more cytotoxic agents.

In an embodiment, the fusion protein of the invention is administered systemically in the methods described herein. In an embodiment, the fusion protein of the invention is administered locally in the methods described herein. In an embodiment, the fusion protein of the invention is administered directly to the tumor in the methods described herein, for example by injection or cannulation.

In an embodiment, the agent comprising an IgV-like domain of a TMIGD2 conjugated to a cytotoxic agent of the invention is administered systemically in the methods described herein. In an embodiment, the agent comprising an IgV-like domain of a TMIGD2 conjugated to a cytotoxic agent of the invention is administered locally in the methods described herein. In an embodiment, the agent comprising an IgV-like domain of a TMIGD2 conjugated to a cytotoxic agent of the invention is administered directly to the tumor in the methods described herein, for example by injection or cannulation.

In an embodiment, "determining" as used herein means experimentally determining.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Figure 1A:
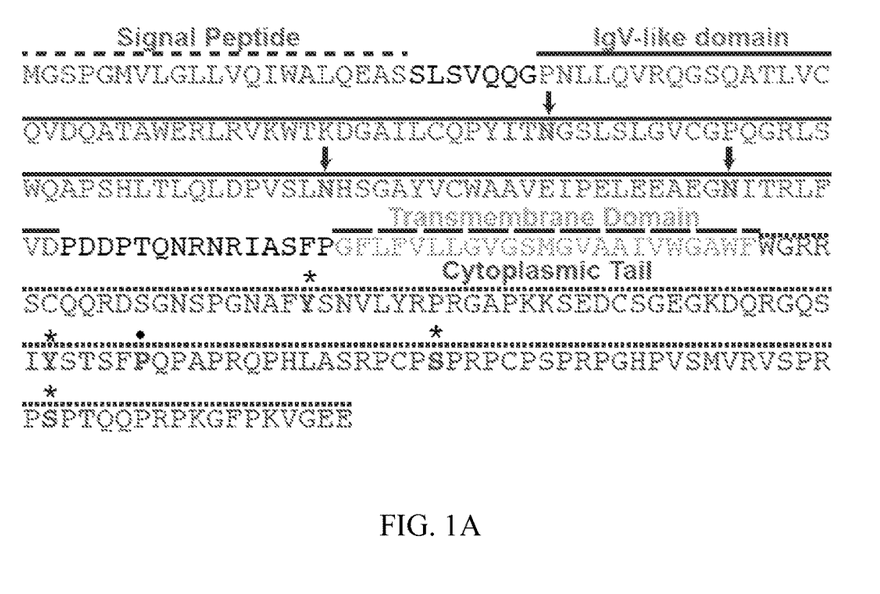
FIG. 1A. Transmembrane and Immunoglobulin Domain Containing 2 (TMIGD2) is an immunoglobulin family member that binds to HHLA2. TMIGD2 is composed of a signal peptide, a single extracellular immunoglobulin domain, transmembrane domain, and a cytoplasmic tail. There are 3 predicted sites of N-linked glycosylation found within the Ig domain (arrows) and four sites of predicted phosphorylation (asterisks) and one potential SH3-binding domain (dot) within the cytoplasmic tail. The whole sequence set forth in FIG. 1A is SEQ ID NO:4.

Identification of immunoglobulin domain-13 containing protein 2 (TMIGD2) as one of the receptors for HHLA2: Receptors for HHLA2 are widely expressed on both naïve and activated T cells as well as dendritic cells, monocytes, and B cells (1). As HHLA2 is a member of the immunoglobulin superfamily and has orthologs in humans and monkeys but not in mice or rats, it was hypothesized the receptors for HHLA2 may belong to the immunoglobulin superfamily and have the same expression pattern due to the co-evolution. From more than 500 members of the immunoglobulin superfamily, a list was compiled of the immunoglobulin family members expressed in humans and monkeys but not in mice or rats. This list was further refined by only including members with predicted transmembrane domains. Their ability to bind to HHLA2 was tested. It was also found that a fusion protein of Transmembrane and Immunoglobulin Domain Containing (2) (TMIGD2, FIG. 1A), the extracellular domain of TMIGD2 linked to the Fc region of human IgG1 (TMIGD2-Ig), bound strongly to 3T3 cells overexpressing HHLA2 (FIG. 1B) but not other human B7 molecules in flow cytometry. TMIGD2 contains an N-terminal signal peptide, an extracellular IgV-like domain, three potential sites for N-linked glycosylation, a transmembrane region, and a cytoplasmic tail with two potential sites for phosphorylation (FIG. 1A). Thus, TMIGD2 was identified as a receptor for HHLA2.

The human TMIGD2-Ig fusion protein (SEQ ID NO:3) was generated with the extracellular domain of TMIGD2 linked to the Fc region of human IgG1. TMIGD2-Ig protein was generated in Drosophila S2 cells and purified using Protein G columns.

Prophetic Example

TMIGD2-Ig is administered to humanized NOD-scid/IL2Rgnull (NSG) mice bearing HHLA2 positive human tumors. It will be seen that the tumors are reduced in size in the animals treated with TMIGD2-Ig compared to controls. In addition, a TMIGD2-drug conjugate is administered to humanized NOD-scid/IL2Rgnull (NSG) mice bearing HHLA2 positive human tumors. It will be seen that the tumors are reduced in size in the animals treated with TMIGD2-drug conjugate compared to controls.

Discussion

Figure 1B:
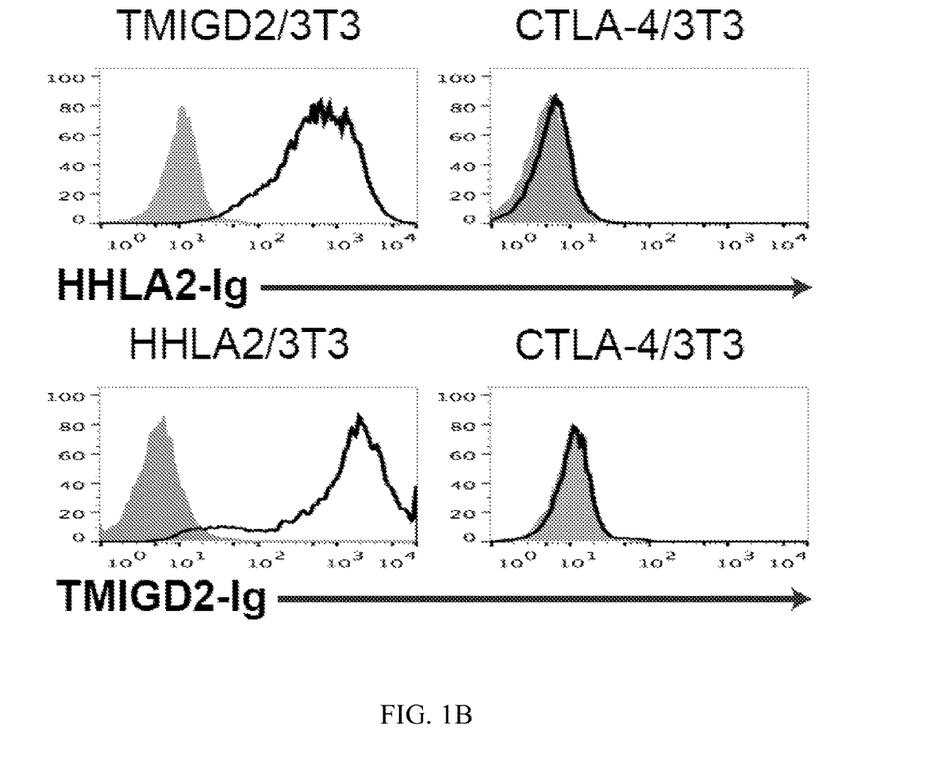
FIG. 1B. HHLA2-Ig binds to TMIGD2-expressing 3T3 cells but not to CTLA-4-expressing 3T3 cells. TMIGD2-Ig binds to HHLA2-expressing 3T3 cells but not to CTLA-4-expressing 3T3 cells. Cells were stained with HHLA2-Ig or TMIGD2-Ig (open histograms) or control Ig (shaded histograms) followed by anti-human IgG-APC.
Figure 1C:
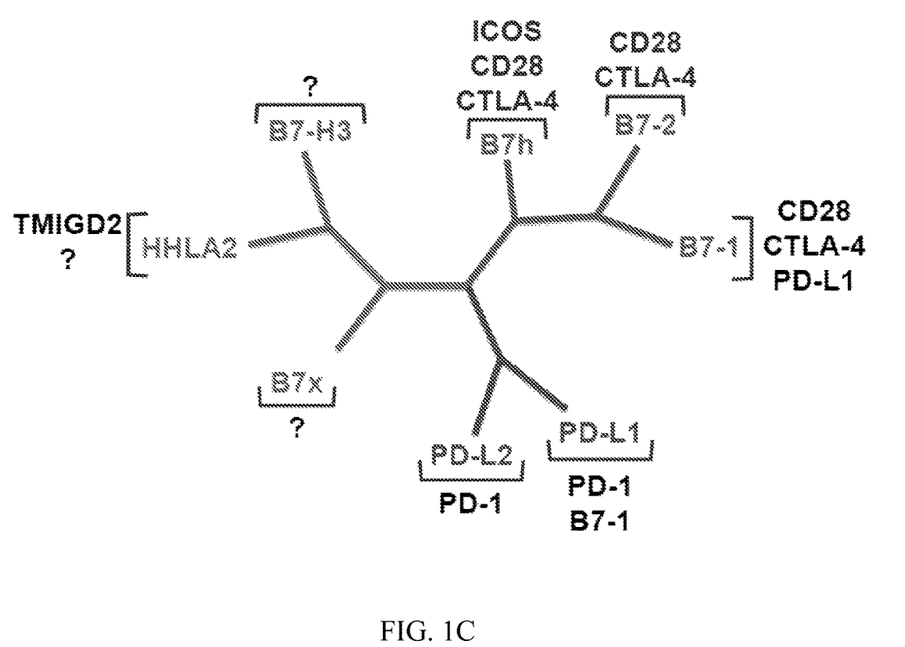
FIG. 1C. Phylogenetic tree of the human B7 and CD28 families. The phylogenetic comparison of human B7 molecules was generated by PAUP and was divided into three groups. Receptors for human B7 molecules are also shown. TMIGD2 and HHLA2 are in the group 3.

TMIDG2 and its derivatives as blockers or binders of HHLA2 for immunotherapies: Given the new finding that TMIGD2 very strongly binds HHLA2 (FIG. 1), together with the previous findings that HHLA2 is an inhibitor of the human immune system (1) and that many human cancers over-express HHLA2 as a novel immunosuppressive mechanism (10), TMIGD2 and its derivatives can be used as blockers or binders of HHLA2 for immunotherapies of cancers and other diseases. There are at least two possible mechanisms by which the TMIGD2 protein and its derivatives can treat cancers: (1) TMIGD2 protein and its derivatives can bind cancer-expressed HHLA2 and therefore enhance anti-tumor immunity by blocking HHLA2-mediated immunosuppression; and (2) TMIGD2-drug conjugates and its derivatives-drug conjugates can bind HHLA2 positive human cancer cells and directly kill them. Accordingly, the following are within the scope of the invention:

i) TMIGD2-Ig fusion proteins can be used to treat human cancers by blocking immunosuppression of tumor-expressed HHLA2, including cancers of the breast, lung, thyroid, melanoma, pancreas, ovary, liver, bladder, colon, prostate, kidney, esophagus, leukemia and lymphoma;

ii) derivatives of TMIGD2 protein (such as high-affinity and low-affinity mutants, IgV-like domain of TMIDG2) can be used to treat human cancers by blocking immunosuppression of tumor-expressed HHLA2;

iii) TMIGD2-drug conjugates can be used as new drugs to treat human cancers by directly killing HHLA2 positive cancer cells; and iv) TMIGD2-derivative-drug conjugates can be used as new drugs to treat human cancers by directly killing HHLA2 positive cancer cells.

Materials and Methods

Bioinformatic Analysis: The NCBI database was queried for proteins of the immunoglobulin family with homologues in humans and monkeys, but not in mice or rats. The sequences of the resulting list of proteins were analyzed by various domain-prediction programs to determine if these proteins contained Ig, IgC, IgC-like, IgV, or IgV-like domains. The list was further refined by excluding proteins that did not contain a transmembrane domain. MacVector 10.6. was used for sequence alignment and homology comparison. The phylogenetic tree was generated by PAUP (4.0b10) after removal of significant inserts and trimming C- and N-terminal extensions from sequence alignments. Motifs and domains were analyzed with EMBL-EBI tools, SMART, and CBS Prediction. For gene copy number variations, the cBioPortal for Cancer Genomics database and the Cancer Genome Atlas were analyzed.

Fusion Protein Production and Purification: TMIGD2-Ig fusion protein was prepared by PCR-amplifying the extracellular domain of the protein without the signal peptide. The amplified product was inserted into a human IgG1 Fc tag of plasmid pMT/BiP. Drosophila Schneider 2 cells were co-transfected with this construct and a plasmid inducing hygromycin resistance. The fusion protein was expressed in Express Five serum-free medium (Life Technologies) and purified using Protein G Plus Agarose columns (Pierce). The purity of the fusion protein was confirmed by SDS-PAGE.

Identification of immunoglobulin domain—containing protein 2 (TMIGD2) as one of the receptors for HHLA2: Receptors for HHLA2 are widely expressed on both naïve and activated T cells as well as dendritic cells, monocytes, and B cells. As HHLA2 is a member of the immunoglobulin superfamily and has orthologs in humans and monkeys but not in mice or rats, it was hypothesized that the receptors for HHLA2 may belong to the immunoglobulin superfamily and have the same phylogenetic pattern due to co-evolution.

From more than 500 members of the immunoglobulin superfamily, a list was compiled of the immunoglobulin family members expressed in humans and monkeys but not in mice or rats. This list was further refined by only including members with predicted transmembrane domains. Their ability to bind to HHLA2 was tested. A fusion protein of Transmembrane and Immunoglobulin Domain Containing 2 (TMIGD2), the extracellular domain of TMIGD2 linked to the Fc region of human IgG1 (TMIGD2-Ig), bound strongly to 3T3 cells expressing HHLA2 but not other human B7 molecules in flow cytometry. TMIGD2 contains an N-terminal signal peptide, an extracellular IgV-like domain, three potential sites for N-linked glycosylation, a transmembrane region, and a cytoplasmic tail with two potential sites for phosphorylation. By sequence analysis, it was found that TMIGD2, the immunoglobulin-containing and proline-rich receptor-1 (IGPR-1), and CD28 homologue (CD28H) are the same molecule. IGPR-1 was originally identified as a adhesion molecule involved in angiogenesis, while CD28H was recently reported as a receptor by a high-throughput screen of transmembrane proteins. Thus TMIGD2/IGPR-1/CD28H is one of the receptors for HHLA2.

REFERENCES

1. Zhao, R., et al. HHLA2 is a member of the B7 family and inhibits human CD4 and CD8 T-cell function. *Proceedings of the National Academy of Sciences of the United States of America* 110, 9879-9884 (2013).
2. Scandiuzzi, L., Ghosh, K. & Zang, X. T cell costimulation and coinhibition: genetics and disease. *Discovery Medicine* 12, 119-128 (2011).
3. Zang, X. & Allison, J. P. The B7 family and cancer therapy: costimulation and coinhibition. *Clinical Cancer Research* 13, 5271-5279 (2007).
4. Vincenti, F., Dritselis, A. & Kirkpatrick, P. Belatacept. *Nature reviews. Drug discovery* 10, 655-656 (2011).
5. Fiocco, U., et al. Co-stimulatory modulation in rheumatoid arthritis: the role of (CTLA4-Ig) abatacept. *Autoimmunity Reviews* 8, 76-82 (2008).
6. Barach, Y. S., Lee, J. S. & Zang, X. T cell coinhibition in prostate cancer: new immune evasion pathways and emerging therapeutics. *Trends Mol Med* 17, 47-55 (2011).
7. Janakiram, M., Abadi, Y. M., Sparano, J. A. & Zang, X. T cell coinhibition and immunotherapy in human breast cancer. *Discovery Medicine* 14, 229-236 (2012).
8. Topalian, S. L., et al. Safety, activity, and immune correlates of anti-PD-1 antibody in cancer. *The New England Journal of Medicine* 366, 2443-2454 (2012).
9. Brahmer, J. R., et al. Safety and activity of anti-PD-L1 antibody in patients with advanced cancer. *The New England Journal of Medicine* 366, 2455-2465 (2012).
10. Janakiram M, Chinai J, Fineberg S, Fiser A, Montagna C, Medaverepu R, Castano E, Jeon H, Ohaegbulam K C, Zhao R, Zhao A, Almo S, Sparano J A, Zang X. Expression, clinical significance, and receptor identification of the newest B7 family member HHLA2 protein. Clin Cancer Res. Dec. 30 (2014) [Epub ahead of print].
11. Dall'Acqua W F, Kiener P A, Wu H. Properties of human IgG1s engineered for enhanced binding to the neonatal Fc receptor (FcRn). *J Biol Chem.* 281(33), 23514-24. Epub Jun. 21 (2006).
12. Yeung Y A, Leabman M K, Marvin J S, Qiu J, Adams C W, Lien S, Starovasnik M A, Lowman H B. Engineering human IgG1 affinity to human neonatal Fc receptor: impact of affinity improvement on pharmacokinetics in primates. *J Immunol.* 182(12), 7663-71 (2009).

What is claimed is:

1. A method of treating an HHLA2-bearing tumor in a subject comprising administering to the subject an amount of a fusion protein comprising an IgV-like domain of a TMIGD2 sufficient to treat the HHLA2-bearing tumor, wherein:
the fusion protein comprises consecutive amino acid residues having the sequence set forth in SEQ ID NO:2 or in SEQ ID NO:3.

2. The method of claim 1 wherein the fusion protein comprising an IgV-like domain of a TMIGD2 comprises an Fc portion of an immunoglobulin G.

3. The method of claim 1 wherein the C-terminal residue of the IgV-like domain of a TMIGD2 of the fusion protein is fused via a peptide bond to an N-terminal residue of an Fc portion of an immunoglobulin G.

4. The method of claim 2, wherein the immunoglobulin G has the sequence of a human immunoglobulin G.

5. The method of claim 2, wherein the immunoglobulin G is an immunoglobulin G1.

6. The method of claim 1, wherein the IgV-like domain of the TMIGD2 is conjugated to a cytotoxic agent, and/or wherein the fusion protein is administered in combination with radiation therapy.

7. The method of claim 1, wherein the IgV-like domain of the TMIGD2 comprises consecutive amino acid residues having the sequence set forth in SEQ ID NO:5.

8. The method of claim 1, wherein administration of the fusion protein inhibits immunosuppression by the HHLA2-bearing tumor.

9. The method of claim 1, wherein the HHLA2 of the HHLA2-bearing tumor is a human HHLA2.

10. The method of claim 1, wherein the HHLA2-bearing tumor is a tumor of a breast, lung, thyroid, melanoma, pancreas, ovary, liver, bladder, colon, prostate, kidney, or esophagus, or is a hematological tumor.

11. The method of claim 10, wherein the HHLA2-bearing tumor is a hematological tumor and is a leukemia or a lymphoma.

12. The method of claim 10, wherein the HHLA2-bearing tumor is a tumor of the breast and is a triple negative breast cancer.

13. The method of claim 1, wherein the fusion protein comprises consecutive amino acid residues having the sequence set forth in SEQ ID NO:2.

14. The method of claim 1, wherein the fusion protein comprises consecutive amino acid residues having the sequence set forth in SEQ ID NO:3.

* * * * *

SEQUENCE LISTING

<160> NUMBER OF SEQ ID NOS: 8

<210> SEQ ID NO 1
<211> LENGTH: 414
<212> TYPE: PRT
<213> ORGANISM: Artificial Sequence
<220> FEATURE:
<223> OTHER INFORMATION: fusion protein based on human sequence

<400> SEQUENCE: 1

-continued

```
Met Lys Ala Gln Thr Ala Leu Ser Phe Phe Leu Ile Leu Ile Thr Ser
  1               5                  10                  15

Leu Ser Gly Ser Gln Gly Ile Phe Pro Leu Ala Phe Phe Ile Tyr Val
              20                  25                  30

Pro Met Asn Glu Gln Ile Val Ile Gly Arg Leu Asp Glu Asp Ile Ile
          35                  40                  45

Leu Pro Ser Ser Phe Glu Arg Gly Ser Glu Val Val Ile His Trp Lys
 50                  55                  60

Tyr Gln Asp Ser Tyr Lys Val His Ser Tyr Tyr Lys Gly Ser Asp His
 65                  70                  75                  80

Leu Glu Ser Gln Asp Pro Arg Tyr Ala Asn Arg Thr Ser Leu Phe Tyr
              85                  90                  95

Asn Glu Ile Gln Asn Gly Asn Ala Ser Leu Phe Phe Arg Arg Val Ser
         100                 105                 110

Leu Leu Asp Glu Gly Ile Tyr Thr Cys Tyr Val Gly Thr Ala Ile Gln
     115                 120                 125

Val Ile Thr Asn Lys Val Val Leu Lys Val Gly Val Phe Leu Thr Pro
 130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
             165                 170                 175

Thr Pro Ile Ser Glu Asn Asn Met Glu Glu Thr Gly Ser Leu Asp Ser
            180                 185                 190

Phe Ser Ile Asn Ser Pro Leu Asn Ile Thr Gly Ser Asn Ser Ser Tyr
         195                 200                 205

Glu Cys Thr Ile Glu Asn Ser Leu Leu Lys Gln Thr Trp Thr Gly Arg
     210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
             245                 250                 255

Lys Val Thr Trp Ser Arg Met Lys Ser Gly Thr Phe Ser Val Leu Ala
            260                 265                 270

Tyr Tyr Leu Ser Ser Ser Gln Asn Thr Ile Ile Asn Glu Ser Arg Phe
         275                 280                 285

Ser Trp Asn Lys Glu Leu Ile Asn Gln Ser Asp Phe Ser Met Asn Leu
     290                 295                 300

Met Asp Leu Asn Leu Ser Asp Ser Gly Glu Tyr Leu Cys Asn Ile Ser
305                 310                 315                 320

Ser Asp Glu Tyr Thr Leu Leu Thr Ile His Thr Val His Val Glu Pro
             325                 330                 335

Ser Gln Glu Thr Ala Ser His Asn Lys Gly Leu Trp Ile Leu Val Pro
            340                 345                 350

Ser Ala Ile Leu Ala Ala Phe Leu Leu Ile Trp Ser Val Lys Cys Cys
         355                 360                 365

Arg Ala Gln Leu Glu Ala Arg Arg Ser Arg His Pro Ala Asp Gly Ala
     370                 375                 380

Gln Gln Glu Arg Cys Cys Val Pro Pro Gly Glu Arg Cys Pro Ser Ala
385                 390                 395                 400

Pro Asp Asn Gly Glu Glu Asn Val Pro Leu Ser Gly Lys Val
             405                 410
```

```
<210> SEQ ID NO 2
<211> LENGTH: 361
<212> TYPE: PRT
<213> ORGANISM: Artificial Sequence
<220> FEATURE:
<223> OTHER INFORMATION: Fusion protein based on human sequence

<400> SEQUENCE: 2

Pro Asn Leu Leu Gln Val Arg Gln Gly Ser Gln Ala Thr Leu Val Cys
1               5                   10                  15

Gln Val Asp Gln Ala Thr Ala Trp Glu Arg Leu Arg Val Lys Trp Thr
                20                  25                  30

Lys Asp Gly Ala Ile Leu Cys Gln Pro Tyr Ile Thr Asn Gly Ser Leu
            35                  40                  45

Ser Leu Gly Val Cys Gly Pro Gln Gly Arg Leu Ser Trp Gln Ala Pro
        50                  55                  60

Ser His Leu Thr Leu Gln Leu Asp Pro Val Ser Leu Asn His Ser Gly
65                  70                  75                  80

Ala Tyr Val Cys Trp Ala Ala Val Glu Ile Pro Glu Leu Glu Glu Ala
                85                  90                  95

Glu Gly Asn Ile Thr Arg Leu Phe Val Asp Pro Asp Asp Pro Thr Gln
            100                 105                 110

Asn Arg Asn Arg Ile Ala Ser Phe Gly Gly Arg Ser Lys Thr Ser Gly
        115                 120                 125

Ser Glu Pro Lys Ser Cys Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360
```

<210> SEQ ID NO 3
<211> LENGTH: 367
<212> TYPE: PRT
<213> ORGANISM: Homo sapiens

<400> SEQUENCE: 3

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
            20                  25                  30

Leu Arg Val Lys Trp Thr Lys Asp Gly Ala Ile Leu Cys Gln Pro Tyr
        35                  40                  45

Ile Thr Asn Gly Ser Leu Ser Leu Gly Val Cys Gly Pro Gln Gly Arg
    50                  55                  60

Leu Ser Trp Gln Ala Pro Ser His Leu Thr Leu Gln Leu Asp Pro Val
65                  70                  75                  80

Ser Leu Asn His Ser Gly Ala Tyr Val Cys Trp Ala Ala Val Glu Ile
                85                  90                  95

Pro Glu Leu Glu Glu Ala Glu Gly Asn Ile Thr Arg Leu Phe Val Asp
            100                 105                 110

Pro Asp Asp Pro Thr Gln Asn Arg Asn Arg Ile Ala Ser Phe Gly Gly
        115                 120                 125

Arg Ser Lys Thr Ser Gly Ser Glu Pro Lys Ser Cys Asp Lys Thr His
    130                 135                 140

Thr Cys Pro Pro Cys Pro Ala Pro Glu Leu Leu Gly Gly Pro Ser Val
145                 150                 155                 160

Phe Leu Phe Pro Pro Lys Pro Lys Asp Thr Leu Met Ile Ser Arg Thr
                165                 170                 175

Pro Glu Val Thr Cys Val Val Val Asp Val Ser His Glu Asp Pro Glu
            180                 185                 190

Val Lys Phe Asn Trp Tyr Val Asp Gly Val Glu Val His Asn Ala Lys
        195                 200                 205

Thr Lys Pro Arg Glu Glu Gln Tyr Asn Ser Thr Tyr Arg Val Val Ser
    210                 215                 220

Val Leu Thr Val Leu His Gln Asp Trp Leu Asn Gly Lys Glu Tyr Lys
225                 230                 235                 240

Cys Lys Val Ser Asn Lys Ala Leu Pro Ala Pro Ile Glu Lys Thr Ile
                245                 250                 255

Ser Lys Ala Lys Gly Gln Pro Arg Glu Pro Gln Val Tyr Thr Leu Pro
            260                 265                 270

Pro Ser Arg Glu Glu Met Thr Lys Asn Gln Val Ser Leu Thr Cys Leu
        275                 280                 285

Val Lys Gly Phe Tyr Pro Ser Asp Ile Ala Val Glu Trp Glu Ser Asn
    290                 295                 300

Gly Gln Pro Glu Asn Asn Tyr Lys Thr Thr Pro Pro Val Leu Asp Ser
305                 310                 315                 320

Asp Gly Ser Phe Phe Leu Tyr Ser Lys Leu Thr Val Asp Lys Ser Arg
                325                 330                 335

Trp Gln Gln Gly Asn Val Phe Ser Cys Ser Val Met His Glu Ala Leu
            340                 345                 350

His Asn His Tyr Thr Gln Lys Ser Leu Ser Leu Ser Pro Gly Lys
        355                 360                 365

<210> SEQ ID NO 4

```
<211> LENGTH: 282
<212> TYPE: PRT
<213> ORGANISM: Homo sapiens

<400> SEQUENCE: 4

Met Gly Ser Pro Gly Met Val Leu Gly Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Pro Thr Gln Asn Arg Asn Arg
    130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
            180                 185                 190

Ser Asn Val Leu Tyr Arg Pro Arg Gly Ala Pro Lys Lys Ser Glu Asp
        195                 200                 205

Cys Ser Gly Glu Gly Lys Asp Gln Arg Gly Gln Ser Ile Tyr Ser Thr
    210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
                260                 265                 270

Pro Lys Gly Phe Pro Lys Val Gly Glu Glu
            275                 280

<210> SEQ ID NO 5
<211> LENGTH: 106
<212> TYPE: PRT
<213> ORGANISM: Homo sapiens

<400> SEQUENCE: 5

Pro Asn Leu Leu Gln Val Arg Gln Gly Ser Gln Ala Thr Leu Val Cys
1               5                   10                  15

Gln Val Asp Gln Ala Thr Ala Trp Glu Arg Leu Arg Val Lys Trp Thr
            20                  25                  30

Lys Asp Gly Ala Ile Leu Cys Gln Pro Tyr Ile Thr Asn Gly Ser Leu
        35                  40                  45

Ser Leu Gly Val Cys Gly Pro Gln Gly Arg Leu Ser Trp Gln Ala Pro
    50                  55                  60
```

```
Ser His Leu Thr Leu Gln Leu Asp Pro Val Ser Leu Asn His Ser Gly
65                  70                  75                  80

Ala Tyr Val Cys Trp Ala Ala Val Glu Ile Pro Glu Leu Glu Glu Ala
                85                  90                  95

Glu Gly Asn Ile Thr Arg Leu Phe Val Asp
            100                 105

<210> SEQ ID NO 6
<211> LENGTH: 120
<212> TYPE: PRT
<213> ORGANISM: Homo sapiens

<400> SEQUENCE: 6

Pro Asn Leu Leu Gln Val Arg Gln Gly Ser Gln Ala Thr Leu Val Cys
1               5                   10                  15

Gln Val Asp Gln Ala Thr Ala Trp Glu Arg Leu Arg Val Lys Trp Thr
                20                  25                  30

Lys Asp Gly Ala Ile Leu Cys Gln Pro Tyr Ile Thr Asn Gly Ser Leu
            35                  40                  45

Ser Leu Gly Val Cys Gly Pro Gln Gly Arg Leu Ser Trp Gln Ala Pro
50                  55                  60

Ser His Leu Thr Leu Gln Leu Asp Pro Val Ser Leu Asn His Ser Gly
65                  70                  75                  80

Ala Tyr Val Cys Trp Ala Ala Val Glu Ile Pro Glu Leu Glu Glu Ala
                85                  90                  95

Glu Gly Asn Ile Thr Arg Leu Phe Val Asp Pro Asp Asp Pro Thr Gln
            100                 105                 110

Asn Arg Asn Arg Ile Ala Ser Phe
        115                 120

<210> SEQ ID NO 7
<211> LENGTH: 5
<212> TYPE: PRT
<213> ORGANISM: Artificial Sequence
<220> FEATURE:
<223> OTHER INFORMATION: synthesized linker sequence

<400> SEQUENCE: 7

Gly Gly Gly Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: synthesized linker sequence

<400> SEQUENCE: 8

Glu Ala Ala Ala Lys
1               5
```